(12) United States Patent
Yamamoto et al.

(10) Patent No.: US 6,548,678 B1
(45) Date of Patent: Apr. 15, 2003

(54) METHOD FOR PRODUCING 5-PHENOXYCARBONYLBENZOTRIAZOLE

(75) Inventors: Keiko Yamamoto, Toyonaka (JP); Takashi Kamikawa, Nara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/252,552

(22) Filed: Sep. 24, 2002

(30) Foreign Application Priority Data

Sep. 28, 2001 (JP) ........................................ 2001-299012

(51) Int. Cl.$^7$ .............................................. C07D 249/18
(52) U.S. Cl. ........................................ 548/261; 548/260
(58) Field of Search ................................. 548/261, 260

(56) References Cited

FOREIGN PATENT DOCUMENTS

| DE | 1 288 094 | 10/1969 |
| GB | 902132 | 7/1962 |
| JP | 55-100339 A | 7/1980 |

OTHER PUBLICATIONS

Maekawa, "Preparation of 5–phenoxycarbonylbenzotriazole" CA 131: 243273 (1999).*

* cited by examiner

*Primary Examiner*—Patricia L. Morris
(74) *Attorney, Agent, or Firm*—Sughrue Mion, PLLC

(57) ABSTRACT

Disclosed is a method for producing 5-phenoxycarbonylbenzotriazole (I):

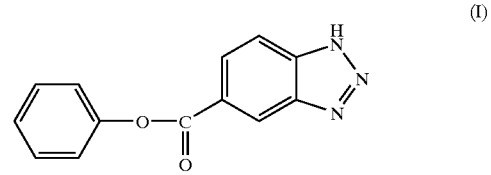

by reacting 1H-benzotriazole-5-carboxylic acid (II):

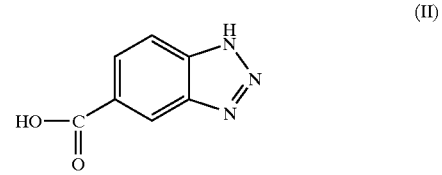

with diphenyl carbonate (III):

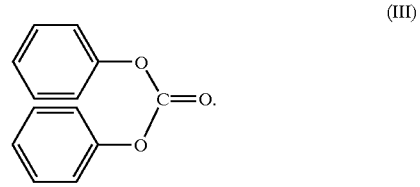

9 Claims, No Drawings

METHOD FOR PRODUCING 5-PHENOXYCARBONYLBENZOTRIAZOLE

FIELD OF THE INVENTION

The present invention relates to a method for producing 5-phenoxycarbonylbenzotriazole.

BACKGROUND OF THE INVENTION

5-Phenoxycarbonylbenzotriazole is a compound of formula (I):

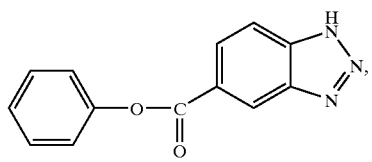

(I)

which is a useful material for the production of photosensitive materials. There was disclosed in Japanese Patent Kokai No. 269,156/99 a method of reacting 1H-benzotriazole-5-carboxylic acid of formula (II):

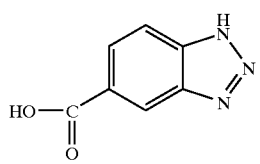

(II)

with triphenyl phosphite.

The method, however, has a problem in that phosphite ester is formed as a by-product in substantially the same amount as that of the desired 5-phenoxycarbonyl-benzotriazole and the treatment thereof was tedious.

SUMMARY OF THE INVENTION

According to the process of the present invention, 5-phenoxycarbonylbenzotriazole of formula (I) can be produced in a good yield from 1H-benzotriazole-5-carboxylic acid (II) and diphenyl carbonate of formula (III):

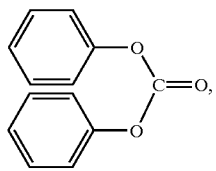

(III)

thereby the amount of a by-product accompanying the reaction is not only reduced but also the treatment thereof is facilitated.

DETAILED DESCRIPTION OF THE INVENTION

The present invention provides a method for producing 5-phenoxycarbonylbenzotriazole, comprising reacting 1H-benzotriazole-5-carboxylic acid with diphenyl carbonate.

The amount of diphenyl carbonate used in the method of the present invention is usually at least one mole, preferably, 5 moles or less, and more preferably, 3 moles or less per one mole of 1H-benzotriazole-5-carboxylic acid.

The reaction of the present invention is usually conducted in the presence of a base or a metal oxide. Examples of the base that may be used in the present invention include an organic and inorganic bases. Examples of the organic base include diisopropylethylamine (pKa=11) N,N'-dimethylaminopyridine (pKa=9.71), 1,4-diazabicyclo[2.2.2]octane (pKa=8.7), N-methylmorpholine (pKa=7.41), imidazole (pKa=6.99), N-methylimidazole (pKa=7.1), pyridine (pKa=5.42), etc. "pKa" values cited in the parentheses above mean an acid dissociation constant of a conjugated acid of each compound. Preferred organic bases are organic bases of which conjugated acid has an acid dissociation constant pKa of 7.2 or more in view of the desired product yield.

Examples of the inorganic base include an alkali metal carbonate such as sodium carbonate, potassium carbonate, sodium hydrogen carbonate, potassium hydrogen carbonate or the like; an alkali metal hydroxide such as lithium hydroxide, sodium hydroxide, or potassium hydroxide; and an alkaline earth metal hydroxide such as magnesium hydroxide, calcium hydroxide, or cesium hydroxide. The metal oxides usable in the present invention include, for example, magnesium oxide, barium oxide, zinc oxide, lead monoxide, or calcium oxide.

A catalytic amount of the base or metal oxide may be used in the reaction, and typically the base or metal oxide is used in an amount of 2 moles or less, preferably, 0.5 mole or less; or usually, at least 0.001 mole, preferably, at least 0.01 mole per mole of 1H-benzotriazole-5-carboxylic acid.

For example, an organic base such as pyridine or N-methylimidazole, which can be present in a liquid form, can be used in an amount of 20 parts by mass, preferably, 7 parts or less by mass, and more preferably, 2 parts or less by mass per one part by mass of 1H-benzotriazole-5-carboxylic acid.

The reaction according to the present invention is usually carried out in a solvent. The base, which is liquid under the reaction conditions, may be used as a solvent. Examples of the solvents that may be used in this reaction include, for example, an aprotic polar solvent such as N,N-dimethylformamide, dimethylsulfoxide, N-methylpyrrolidone, or N,N-dimethylacetamide usually in an amount of 20 parts by mass, preferably, 7 parts or less by mass, and more preferably, 2 parts or less by mass per one part by mass of 1H-benzotriazole-5-carboxylic acid.

The reaction of the present invention is usually conducted by mixing 1H-benzotriazole-5-carboxylic acid with diphenyl carbonate in a solvent, and preferably the base or metal oxide may be used in such a way that the base or metal oxide is added to the mixture of 1H-benzotriazole-5-carboxylic acid, diphenyl carbonate and the solvent. The base, which is liquid under the reaction conditions, can be mixed with 1H-benzotriazole-5-carboxylic acid and diphenyl carbonate without using a solvent.

The reaction of the present invention is usually conducted at 60° C. or higher, preferably, 70° C. or higher; and usually, 160° C. or lower, preferably, 140° C. or lower.

In the reaction, carbon dioxide and phenol are formed as by-products, however, the former can be easily evacuated out of the reaction system.

To obtain 5-phenoxycarbonylbenzotriazole from the resulting reaction mixture, for example, the compound can be obtained by evaporating a reaction solvent out of the mixture, extracting with a suitable solvent, and/or collecting after crystallization with a solvent. The crystallization is usually conducted, for example, by cooling the reaction mixture, or an evaporated mixture thereof dissolved in a suitable solvent, precipitating the desired product under cooling, and collecting the precipitated product by filtration. Typically the crystallization is conducted by using an insufficient solvent, which is usually added to the reaction mixture or an evaporated mixture thereof.

Examples of the insufficient solvent include, for example, an alcohol such as methanol, ethanol, or isopropanol; an aliphatic hydrocarbon such as hexane, or heptane; water; and an aromatic hydrocarbon such as toluene or the like. Preferred are the alcohol and water in view of the filtrability, and more preferred is a mixture of water and the alcohol.

The present invention will be described with reference to the following preferred embodiments but should not be limited thereto:

EXAMPLE 1

N,N-Dimethylformamide (200 g), 1H-benzotriazole-5-carboxylic acid (100 g, 0.61 mole), diphenyl carbonate (157.58 g, 0.74 mole), and sodium carbonate (1.3 g, 0.012 mole) were mixed, heated to 100° C. and stirred at the same temperature for three hours. The resulting reaction mixture contained 143.7 g of 5-phenoxycarbonyl benzotriazole in a yield of 98.0%.

EXAMPLES 2 to 14

N,N-Dimethylformamide (1.88 g), 1H-benzotriazole-5-carboxylic acid (81.6 g, 0.5 mmole), and a metal oxide or a base (an organic or inorganic base) were mixed in an amount as indicated in Table 1, then heated to a temperature as indicated in Table 1 and stirred at the same temperature for five hours. Each of the resulting reaction mixture was analyzed on high-performance liquid chromatography, and the yield of 5-phenoxycarbonylbenzotriazole for each mixture was calculated. The results are in Table 1.

TABLE 1

| Ex. | Metal oxide or base | Amount (mmol) | Temp. (°C.) | Yield (%) |
|---|---|---|---|---|
| | (Metal oxide) | | | |
| 2 | Barium oxide | 0.05 | 100 | 99 |
| 3 | Calcium oxide | 0.05 | 100 | 93 |
| | (Inorganic base) | | | |
| 4 | Barium hydroxide | 0.01 | 80 | 94 |
| 5 | Sodium hydroxide | 0.01 | 80 | 97 |
| 6 | Potassium hydroxide | 0.01 | 80 | 95 |
| 7 | Lithium hydroxide | 0.01 | 80 | 92 |
| | (Organic base) | | | |
| 8 | Diisopropylethylamine (pKa = 11) | 0.01 | 80 | 90 |
| 9 | N,N'-Dimethylaminopyrydine (pKa = 9.71) | 0.01 | 100 | 96 |
| 11 | 1,4-Diazabicyclo [2.2.2] octane (pKa = 8.7) | 0.01 | 80 | 96 |
| 12 | N-methylmorpholine (pKa = 7.41) | 0.01 | 80 | 96 |
| 13 | Imidazole (pKa = 6.99) | 0.01 | 100 | 27 |
| 14 | Pyridine (pKa=5.42) | 0.75 | 100 | 88 |

EXAMPLE 15

The Experiment of Example 1 was repeated in a half scale. After completion of the reaction, about half amount of the solvent in the resulting reaction mixture was evaporated. To the remaining mixture were dropwise added at 60° C. 3.5 parts by weight of a mixture of water and methanol in a ratio of 30:5 per part by weight of 1H-Benzotriazole-5-carboxylic acid used in the reaction, cooled to 20° C., and precipitated crystals were collected to give the desired product (purity: 98.8%) in a yield of 89.3%, in which product phenol was not detected.

Comparative Example 1

1H-Benzotriazole-5-carboxylic acid (10 g, 61.3 mmole) toluene (26.5 g), and p-toluenesulfonate monohydrate (17.48 g, 101.5 mmol) were mixed, and heated up to 110° C. Thereafter, 22 cm$^3$ of toluene were removed. Then, triphenyl phosphite (21.3 g, 68.6 mmol) was added dropwise into the resulting mixture over 30 min at the same temperature. After completion of the addition, the reaction mixture was heated up to about 130° C. and further reacted at the same temperature for six hours. The resulting mixture contained 11.59 g of 5-phenoxycarbonyl benzotriazole in a yield of 79.0%.

Even though carbon dioxide and phenol are formed as by-products according to the method of the present invention, they are readily disposable compounds.

According to the present invention, 5-phenoxycarbonylbenzotriazole is produced from 1H-benzotriazole-5-carboxylic acid in a relatively simple manner.

While what are at present considered to be the preferred embodiments of the invention have been described, it will be understood that various modifications may be made therein, and the appended claims are intended to cover all such modifications as fall within the true spirits and scope of the invention.

What is claimed is:
1. A method for producing 5-phenoxycarbonylbenzotriazole, comprising reacting 1H-benzotriazole-5-carboxylic acid with diphenyl carbonate.

2. A method according to claim 1, wherein said diphenyl carbonate is used in an amount of at least one mole per mole of 1H-benzotriazole-5-carboxylic acid.

3. A method according to claim 1, wherein the reactants are reacted in the presence of a base or a metal oxide.

4. A method according to claim 3, wherein said base is an organic or inorganic base.

5. A method according to claim 4, wherein said organic base is an organic base of which conjugated acid has an acid dissociation constant pKa of 7.2 or more.

6. A method according to claim 4, wherein said inorganic base is an alkali metal carbonate, alkali metal hydroxide, or alkaline earth metal hydroxide.

7. A method according to claim 3, wherein said metal oxide is magnesium oxide, barium oxide, zinc oxide, lead monoxide, or calcium oxide.

8. A method according to claim 1, wherein the reacting of 1H-benzotriazole-5carboxylic acid with diphenyl carbonate is conducted in a solvent.

9. A method according to claim 8, wherein said solvent is an aprotic polar solvent.

* * * * *